United States Patent
Becker et al.

(10) Patent No.: US 6,602,841 B1
(45) Date of Patent: Aug. 5, 2003

(54) GRANULE WITH HYDRATED BARRIER MATERIAL

(75) Inventors: Nathaniel T. Becker, Burlingame, CA (US); Robert I. Christensen, Jr., Pinole, CA (US); Alfred L. Gaertner, San Bruno, CA (US); Mahmood M. Ghani, Milpitas, CA (US); Douglas A. Dale, Pacifica, CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

(21) Appl. No.: 09/581,717

(22) PCT Filed: Dec. 21, 1998

(86) PCT No.: PCT/US98/27214

§ 371 (c)(1),
(2), (4) Date: Jun. 16, 2000

(87) PCT Pub. No.: WO99/32595

PCT Pub. Date: Jul. 1, 1999

Related U.S. Application Data

(60) Provisional application No. 60/068,382, filed on Dec. 20, 1997.

(51) Int. Cl.[7] ............................ C11D 7/42; C11D 3/386; C12N 9/98; C12N 11/14
(52) U.S. Cl. ................... 510/392; 510/441; 510/530; 435/176; 435/187
(58) Field of Search ................ 510/392, 320, 510/441, 349, 530; 435/176, 187

(56) References Cited

U.S. PATENT DOCUMENTS

| | | | | |
|---|---|---|---|---|
| 3,650,961 A | * | 3/1972 | Hudson | 510/530 |
| 3,714,051 A | * | 1/1973 | Milesi et al. | 510/530 |
| 3,764,542 A | * | 10/1973 | Natali et al. | 510/530 |
| 3,773,671 A | * | 11/1973 | Hussain | 510/530 |
| 4,106,991 A | | 8/1978 | Markussen et al. | |
| 4,381,247 A | * | 4/1983 | Nakagawa et al. | 510/530 |
| 4,664,917 A | * | 5/1987 | Meyer | 426/2 |
| 4,689,297 A | | 8/1987 | Good et al. | |
| 4,740,469 A | | 4/1988 | Nishinaka et al. | |
| 4,760,025 A | | 7/1988 | Estell et al. | |
| 4,965,012 A | * | 10/1990 | Olson | 510/221 |
| 5,324,649 A | | 6/1994 | Arnold et al. | |
| 5,814,501 A | | 9/1998 | Becker et al. | |
| 5,879,920 A | * | 3/1999 | Dale et al. | 435/187 |

FOREIGN PATENT DOCUMENTS

| | | |
|---|---|---|
| DE | 40 41 752 A1 | 6/1992 |
| DE | 43 44 215 A1 | 6/1995 |
| EP | 0206417 A2 * | 12/1986 |
| EP | 0 130 756 B1 | 6/1991 |
| WO | WO 91/06637 | 5/1991 |
| WO | WO 91/09941 | 7/1991 |
| WO | WO 97/12958 | 4/1997 |
| WO | WO 98/45395 | 10/1998 |
| WO | WO 99/32595 | 7/1999 |
| WO | WO 99/32612 | 7/1999 |
| WO | WO 99/32613 | 7/1999 |

OTHER PUBLICATIONS

Derwent Publications Ltd., London, GB; Database WPI, Week 8501, AN 85–003970, JP 59 204697 A (Kao Corp.) Nov. 20, 1984 (XP002102119).

* cited by examiner

*Primary Examiner*—Lorna M. Douyon
(74) *Attorney, Agent, or Firm*—Genencor International, Inc.

(57) ABSTRACT

A granule having high stability and low dust is described. The granule includes a hydrated barrier material having moderate or high water activity. Also described are methods of producing the granules.

21 Claims, No Drawings

GRANULE WITH HYDRATED BARRIER MATERIAL

This application claims benefit of provisional application Ser. No. 60/068,382 filed Dec. 20, 1997.

BACKGROUND OF THE INVENTION

Recently the use of enzymes, especially of microbial origin, has become more and more common. Enzymes are used in several industries including, for example, the starch industry, the dairy industry, and the detergent industry. It is well known in the detergent industry that the use of enzymes, particularly proteolytic enzymes, has created industrial hygiene concerns for detergent factory workers, particularly due to the health risks associated with dustiness of the available enzymes.

Since the introduction of enzymes into the detergent business, many developments in the granulation and coating of enzymes have been offered by the industry. See for example the following patents relating to enzyme granulation.

U.S. Pat. No. 4,106,991 describes an improved formation of enzyme granules by including within the composition undergoing granulation, finely divided cellulose fibers in an amount of 2–40% w/w based on the dry weight of the whole composition. In addition, this patent describes that waxy substances can be used to coat the particles of the granulate.

U.S. Pat. No. 4,689,297 describes enzyme containing particles which comprise a particulate, water dispersible core which is 150–2,000 microns in its longest dimension, a uniform layer of enzyme around the core particle which amounts to 10%–35% by weight of the weight of the core particle, and a layer of macro-molecular, film-forming, water soluble or dispersible coating agent uniformly surrounding the enzyme layer wherein the combination of enzyme and coating agent is from 25–55% of the weight of the core particle. The core material described in this patent includes clay, a sugar crystal enclosed in layers of corn starch which is coated with a layer of dextrin, agglomerated potato starch, particulate salt, agglomerated trisodium citrate, pan crystallized NaCl flakes, bentonite granules or prills, granules containing bentonite, Kaolin and diatomaceous earth or sodium citrate crystals. The film forming material may be a fatty acid ester, an alkoxylated alcohol, a polyvinyl alcohol or an ethoxylated alkylphenol.

U.S. Pat. No. 4,740,469 describes an enzyme granular composition consisting essentially of from 1–35% by weight of an enzyme and from 0.5–30% by weight of a synthetic fibrous material having an average length of from 100–500 micron and a fineness in the range of from 0.05–0.7 denier, with the balance being an extender or filler. The granular composition may further comprise a molten waxy material, such as polyethylene glycol, and optionally a colorant such as titanium dioxide.

U.S. Pat. No. 5,254,283 describes a particulate material which has been coated with a continuous layer of a non-water soluble, warp size polymer. U.S. Pat. No. 5,324,649 describes enzyme-containing granules having a core, an enzyme layer and an outer coating layer. The enzyme layer and, optionally, the core and outer coating layer contain a vinyl polymer.

WO 91/09941 describes an enzyme containing preparation whereby at least 50% of the enzymatic activity is present in the preparation as enzyme crystals. The preparation can be either a slurry or a granulate.

WO 97/12958 discloses a microgranular enzyme composition. The granules are made by fluid-bed agglomeration which results in granules with numerous carrier or seed particles coated with enzyme and bound together by a binder.

However, even in light of these developments offered by the industry (as described above) there is a continuing need for low-dust enzyme granules which have additional beneficial characteristics. Additional beneficial characteristics needed in the enzyme granulation industry are low-residue granule formulations (where low residue is defined as a reduced tendency to leave noticeable undissolved residues on clothes or other material), and improved stability formulations. Accomplishing all these desired characteristics simultaneously is a particularly challenging task since, for example, many delayed release or low-dust agents such as fibrous cellulose or warp size polymers leave behind insoluble residues.

Therefore, it is an object of the present invention to provide low-dust, low residue, highly soluble enzyme granules having increased stability. It is another object of the present invention to provide processes which afford the formation of such improved granules.

SUMMARY OF THE INVENTION

One embodiment of the present invention is a granule that includes a protein core and a hydrated barrier material with moderate or high water activity. The hydrated barrier material can be in one or more layers and/or can be included in the protein core.

A further embodiment of the present invention is a granule that includes an enzyme core and a hydrated barrier material with moderate or high water activity. The hydrated barrier material can be in one or more layers and/or can be included in the enzyme core.

Another embodiment is a method of producing the above granule.

DETAILED DESCRIPTION OF THE INVENTION

The present invention provides a granule with improved stability having low dust. The granule includes a protein core and a hydrated barrier material with moderate or high water activity.

A "protein core" or an "enzyme core" can be homogenous such as that described in U.S. patent application Ser. No. 08/995,457, now abandoned, or layered as described in U.S. Pat. No. 5,324,649.

Proteins that are within the scope of the present invention include pharmaceutically important proteins such as hormones or other therapeutic proteins and industrially important proteins such as enzymes.

Any enzyme or combination of enzymes may be used in the present invention. Preferred enzymes include those enzymes capable of hydrolyzing substrates, e.g. stains. These enzymes are known as hydrolases which include, but are not limited to, proteases (bacterial, fungal, acid, neutral or alkaline), amylases (alpha or beta), lipases, cellulases and mixtures thereof. Particularly preferred enzymes are subtilisins and cellulases. Most preferred are subtilisins such as described in U.S. Pat. No. 4,760,025, EP Patent 130 756 B1 and EP Patent Application WO 91/06637, which are incorporated herein by reference, and cellulases such as Multifect L250™ and Puradax™, commercially available from Genencor International. Other enzymes that can be used in the present invention include oxidases, transferases, dehydratases, reductases, hemicellulases and isomerases.

As noted, the barrier material can be coated over the protein core in one or more layers or made part of the protein core in order to insulate or to impede transport of water and inactivating substances to the protein. When the barrier material is part of the protein core, it can be dispersed throughout the core or as a layer in the core.

Suitable hydrated barrier materials with moderate or high water activity can include salts of an inorganic or organic acid, sugars, polysaccharides, lipids, proteins or synthetic polymers, preferably salts.

The term "water activity", symbolized $a_w$, refers to the fractional relative humidity of an atmosphere in equilibrium with a solid or liquid phase material, i.e., the ratio of the partial pressure of water vapor to that present above pure water at the same temperature. In all phases between which water distribution has reached equilibrium, it is by definition equal. The term "relative humidity" is generally used to describe the water in the atmosphere or gas phase in equilibrium with the solid, and is expressed as a percentage, with 100% as the relative humidity of pure water in a closed system. Thus, for any water activity value, there is a corresponding relative humidity given by $\%RH=100 * a_w$.

Water activity can be readily measured by methods known in the art, typically by placing a sample of the material inside the temperature-controlled chamber of a water activity meter, such as the Water Activity System Model D2100 available from Rotronic Instrument Corp. (Huntington, N.Y.), and allowing the measurement to reach equilibrium as indicated on the display.

A "hydrated" barrier material contains water in a free or bound form, or a combination of the two. The water of hydration can be added either during or after the coating process. The degree of hydration will be a function of the material itself and the temperature, humidity and drying conditions under which it is applied.

"Moderate or high" water activity includes a water activity of at least 0.25, preferably greater than 0.30, most preferably greater than 0.35. The water activity referred to herein is that of the granule itself once it has the barrier material-but no further coatings-coated onto it. Further coatings may mask accurate measurement of the water activity of the barrier material as a distinct layer.

Without wishing to be bound by theory, it is expected that materials with a water activity greater than 0.25 will have a reduced driving force for picking up water under storage conditions in which the relative humidity is greater than 25%. Most climates have relative humidities above 25%. Many detergents have water activities in the range of about 0.3 to 0.4. If the water activity of the granule is actually higher than that of the surrounding detergent or storage climate, the driving force for pick up of water by the granule should be eliminated, and in fact water may be given up by the granule to its surroundings. Even if the water activity of the granule is lower than that of the detergent or the corresponding relative humidity, the water present in the barrier layer would act as a shield limiting the amount of water and hence in activating substances being picked up by the granule and affecting the protein core.

In the case of salt hydrates, the hydrated material is a crystalline salt hydrate with bound water(s) of crystallization. The hydrate should be chosen and applied in a manner such that the resulting coated granule will have a water activity in excess of 0.25, or as high as possible while still providing a granule which is dry to the touch. By applying a salt hydrate, or any other suitable hydrated barrier material, in such a manner, as noted above, one expects that this would eliminate any driving force for further uptake of water by the granule. As an important consequence, the driving force for transport of substances which may be detrimental to enzyme activity, such as perborate or peroxide anion, is removed. Without water as a vehicle, these substances are less likely to penetrate the enzyme core. Empirical data demonstrates that enzyme activity in the granule is substantially enhanced by coating the enzyme core with stable salt hydrates.

Preferred salts include magnesium sulfate heptahydrate, zinc sulfate heptahydrate, copper sulfate pentahydrate, sodium phosphate dibasic heptahydrate, magnesium nitrate hexahydrate, sodium borate decahydrate, sodium citrate dihydrate and magnesium acetate tetrahydrate.

The granules of the present invention can also comprise one or more coating layers. For example, such coating layers may be one or more intermediate coating layers, or such coating layers may be one or more outside coating layers or a combination thereof. Coating layers may serve any of a number of functions in a granule composition, depending on the end use of the granule. For example, coatings may render the protein resistant to oxidation by bleach, bring about the desirable rates of dissolution upon introduction of the granule into an aqueous medium, or provide a barrier against ambient moisture in order to enhance the storage stability of the enzyme and reduce the possibility of microbial growth within the granule.

Suitable coatings include polyvinyl alcohol (PVA), polyvinyl pyrrolidone (PVP), cellulose derivatives such as methylcellulose, hydroxypropylmethyl cellulose, hydroxycellulose, ethylcellulose, carboxymethyl cellulose, hydroxypropyl cellulose, polyethylene glycol, polyethylene oxide, chitosan, gum arabic, xanthan, carrageenan, latex polymers, and enteric coatings. Furthermore, coating agents may be used in conjunction with other active agents of the same or different categories.

Suitable PVAs for incorporation in the coating layer(s) of the granule include partially hydrolyzed, fully hydrolyzed and intermediately hydrolyzed PVAs having low to high degrees of viscosity. Preferably, the outer coating layer comprises partially hydrolyzed PVA having low viscosity. Other vinyl polymers which may be useful include polyvinyl acetate and polyvinyl pyrrolidone. Useful copolymers include, for example, PVA-methylmethacrylate copolymer and PVP-PVA copolymer.

The coating layers of the present invention may further comprise one or more of the following: plasticizers, extenders, lubricants, pigments, and optionally additional enzymes. Suitable plasticizers useful in the coating layers of the present invention are plasticizers including, for example, polyols such as sugars, sugar alcohols, or polyethylene glycols (PEGs), urea, glycol, propylene glycol or other known plasticizers such as triethyl citrate, dibutyl or dimethyl phthalate or water. Suitable pigments useful in the coating layers of the present invention include, but are not limited to, finely divided whiteners such as titanium dioxide or calcium carbonate or colored pigments or dyes or a combination thereof. Preferably such pigments are low residue pigments upon dissolution. Suitable extenders include sugars such as sucrose or starch hydrolysates such as maltodextrin and corn syrup solids, clays such as kaolin and bentonite, and talc. Suitable lubricants include nonionic surfactants such as Neodol, tallow alcohols, fatty acids, fatty acid salts such as magnesium stearate and fatty acid esters.

The outer coating layer of the present invention preferably comprises between about 1–25% by weight of the coated granule.

Adjunct ingredients may be added to the granules of the present invention. Adjunct ingredients may include: metallic salts; solubilizers; activators; antioxidants; dyes; inhibitors; binders; fragrances; enzyme protecting agents/scavengers such as ammonium sulfate, ammonium citrate, urea, guanidine hydrochloride, guanidine carbonate, guanidine sulfamate, thiourea dioxide, monoethanolamine, diethanolamine, triethanolamine, amino acids such as glycine, sodium glutamate and the like, proteins such as bovine serum albumin, casein and the like etc.; surfactants including anionic surfactants, ampholytic surfactants, nonionic surfactants, cationic surfactants and long-chain fatty acid salts; builders; alkalis or inorganic electrolytes; bleaching agents; bluing agents and fluorescent dyes and whiteners; and caking inhibitors.

The granules described herein may be made by methods known to those skilled in the art of enzyme granulation, including pan-coating, fluid-bed coating, fluid-bed agglomeration, prilling, disc granulation, spray drying, extrusion, centrifugal extrusion, spheronization, drum granulation, high shear agglomeration, or combinations of these techniques.

The following examples are representative and not intended to be limiting. One skilled in the art could choose other proteins, protein cores, enzymes, enzyme cores, seed particles, methods and coating agents based on the teachings herein.

EXAMPLES

Example 1.

Stability of Magnesium Sulfate Coated Protease Granules

A. In a Deseret 60 fluidized bed coater, 54.1 kg of sucrose/starch non pareil seeds were charged and fluidized. Onto these cores, 75.8 kg of protease UF concentrate containing 62.9 g/kg subtilisin protease were sprayed under the following conditions. (Ranges indicate initial and final values over the course of the specified ramp time):

| Ramp time: | 80 minutes |
|---|---|
| Fluid feed rate | 0.6–1.0 liter/min |
| Atomization pressure | 75 psi |
| Inlet air temperature | 85–92 degrees C. |
| Outlet air temperature | 50 degrees C. |
| Fluidization air rate | 18 m3/min |

A solution of magnesium sulfate was prepared by adding 22.2 kg of magnesium sulfate heptahydrate into 22.2 kg of water, and this was sprayed onto the enzyme-coated cores under the following conditions in order to provide that 20% of the final granule would be magnesium sulfate heptahydrate, with care being taken to keep the bed temperature close to, but slightly below, 50 degrees C.:

| Ramp time: | 40 minutes |
|---|---|
| Fluid feed rate | 0.6–1.7 liter/min |
| Atomization pressure | 45 psi |
| Inlet air temperature | 70–84 degrees C. |
| Outlet air temperature | 48–50 degrees C. |
| Fluidization air rate | 18 m3/min |

Finally, a polymer coating solution was prepared by dissolving 6.35 kg of Elvanol 51-05 polyvinyl alcohol, 7.94 kg titanium dioxide and 1.59 kg Neodol 23-6.5T nonionic surfactant in 50.12 kg water and spraying over the salt-coated enzyme cores under the following conditions:

| Ramp time: | 10 min, then constant for 100 min |
|---|---|
| Fluid feed rate | 0.6 liter/min |
| Atomization pressure | 75 psi |
| Inlet air temperature | 50 degrees C. |
| Outlet air temperature | 75–80 degrees C. |
| Fluidization air rate | 18 m3/min |

The harvested granules had an enzyme concentration of approximately 40 g/kg.

B. Accelerated Stability Test

The stability of many enzyme granules formulated into bleach-containing detergents is generally excellent, showing generally no more than about 10 to 20% loss in activity over 6 weeks storage at 30 to 37° C. and 70% to 80% R.H. However, to aid in the development and screening of granular formulations, it is desirable to have an accelerated means of determining relative granule stability. The conditions of the accelerated stability test (AST) are far more severe than enzyme granules or detergents would ever encounter in realistic storage or transport. The AST is a "stress test" designed to discriminate differences between formulations which would otherwise not be evident for weeks or months.

In this test, a test detergent base was made from the following ingredients:

| 72% | WFK-1 detergent base | (WFK, Forschunginstitut fuer Reinigungstechnologie e.V., Krefeld, Germany) |
|---|---|---|
| 25% | sodium perborate monohydrate | (Degussa Corp., Allendale Park, New Jersey.) |
| 3% | TAED bleach activator (= tetraacetylethylenediamine) | (Warwick International, Mostyn, UK) |

For each enzyme sample to be tested, three identical tubes were prepared by adding 1 gram of the test base and 30 mg of enzyme granules to a 15 ml conical tube and mixed by inverting the capped tube 5–8 times by hand. A hole was drilled in the tube cap with a 1/16 inch drill bit. One of the three tubes was assayed immediately and the other two were stored in a humidity chamber set at 50° C. and 70%R.H. One of the two stored tubes was assayed after 1 day of storage; the second, after 3 days of storage. Storage stability was reported for Day 1 and Day 3 by dividing the remaining activity by the original activity at Day 0, expressed as a percentage.

The enzyme activity was determined by adding to each tube 30 ml of 0.25M MES pH 5.5 buffer containing 20 µl Catalase HP L5000 (Genencor International, Rochester, N.Y.) and incubating for 40 minutes to inactivate the perborate. After this, the enzyme was assayed by adding 10 µl of the test tube mixture and 10 µl of sAAPF protease substrate to 980 µl of 0.1M Tris pH 8.6, then incubating at 25° C. over 3 minutes, and measuring the optical absorbance at 410 nm. The slope of the absorbance vs. time was then multiplied by the dilution factor and the known extinction coefficient for the specific protease to obtain an enzyme activity as concentration in mg/ml.

The process described in A above was repeated three more times, the only difference being that the outlet air temperature was controlled at a setpoint of 40, 60 and 70 degrees C. in each of the three separate runs. Samples were removed from all four batches after the magnesium sulfate barrier coating had been applied, and water activities of the granules were measure in a Rotronic Water Activity System, as reported in Table 1. Two of the granules, after application of the final polymer coating, were placed in WFK-1 detergent formula and stored in tubes with drilled caps for three days at 50 degrees C. and 70% relative humidity, according to the accelerated stability test method described above. Tubes were withdrawn from the humidity chamber and assayed after 1 day and 3 days. The percent retained activities are reported in Table 1. The results indicate the granules in which magnesium sulfate was coated at 50 degrees C. outlet temperature are significantly more stable than those coated at 70 degrees C., and that the more stable granules had a water activity above 0.35, while the less stable granules had a significantly lower water activity.

TABLE 1

Stability of Magnesium Sulfate Coated Enzyme Granules

| Outlet Temp (C.) | $A_w$ of MgSO4 Coated Protease Cores | Percent Retained Activity of Granules Stored in Bleach Detergent | | |
|---|---|---|---|---|
| | | 0 days | 1 day | 3 days |
| 40 | 0.374 | | | |
| 50 | 0.409 | 100% | 108% | 97% |
| 60 | 0.140 | | | |
| 70 | 0.165 | 100% | 94% | 63% |

Example 2.

Stability of Sodium Citrate Coated Protease Granules

A. In a Vector 60 coater, 25 kg of sucrose/starch nonpareil seeds were fluidized and 30.9 kg of subtilisin protease concentrate with a concentration of 65.9 g/L and 18.3% total solids were sprayed onto the fluidized cores under the following conditions:

| | |
|---|---|
| Ramp time: | 55 minutes |
| Fluid feed rate | 0.5–0.9 liter/min |
| Atomization pressure | 75 psi |
| Inlet air temperature | 60–95 degrees C. |
| Outlet air temperature | 50 degrees C. |
| Fluidization air rate | 24 m3/min |

A solution of trisodium citrate was prepared by adding 13.2 kg of trisodium citrate dihydrate into 19.7 kg of water, and this was sprayed onto the enzyme-coated cores under the following conditions in order to provide that 25% of the final granule would be trisodium citrate dihydrate, with care being taken to keep the bed temperature close to 50 degrees C.:

| | |
|---|---|
| Ramp time: | 23 minutes |
| Fluid feed rate | 0.6–1.9 liter/min |
| Atomization pressure | 75 psi |
| Inlet air temperature | 60–95 degrees C. |
| Outlet air temperature | 50 degrees C. |
| Fluidization air rate | 24 m3/min |

Finally, a polymer coating solution was prepared by dissolving 2.94 kg Methocel HPMC, 0.98 kg polyethylene glycol, molecular weight 600, 2.06 kg titanium dioxide and 0.59 kg Neodol 23-6.5T nonionic surfactant in 55.88 kg water and spraying over the salt-coated enzyme cores under the following conditions:

| | |
|---|---|
| Ramp time: | 10 min, then 80 minutes constant |
| Fluid feed rate | 0.5–0.7 liter/min |
| Atomization pressure | 75 psi |
| Inlet air temperature | 75–80 degrees C. |
| Outlet air temperature | 60 degrees C. |
| Fluidization air rate | 18 m3/min |

The harvested granules had a weight of 49.5 kg and an enzyme concentration of approximately 40 g/kg.

B. The above process was repeated under the same conditions, but the outlet air temperature was controlled at a setpoint of 70 degrees C. Samples were removed from both batches after the sodium citrate barrier coating had been applied, and water activities of the granules were measure in a Rotronic Water Activity System, as reported in Table 2. The two granules, after application of the final polymer coating, were placed in an automatic dish detergent base and stored in sealed tubes for 84 days at 37 degrees C. Tubes were withdrawn from the humidity chamber and assayed after 14, 42 and 84 days. The percent retained activities are reported in Table 2. The results indicate the granules in which sodium citrate was coated at 50 degrees C. outlet temperature are significantly more stable than those coated at 70 degrees C., and that the more stable granules had a water activity above 0.25, while the less stable granules had a significantly lower water activity.

TABLE 2

Stability of Sodium Citrate Coated Enzyme Granules

| Outlet Temp (C.) | $A_w$ of Na3 Citrate Coated Protease Cores | Percent Retained Activity of Granules Stored in Bleach Detergent | | | |
|---|---|---|---|---|---|
| | | 0 days | 14 days | 42 days | 84 days |
| 55 | 0.272 | 100% | 90% | 89% | 87% |
| 70 | 0.059 | 100% | 86% | 81% | 75% |

What is claimed is:

1. A granule comprising a protein core and a barrier salt coated over the protein core, wherein the barrier salt is magnesium sulfate heptahydrate, zinc sulfate heptahydrate, magnesium nitrate hexahydrate, sodium citrate dehydrate or magnesium acetate tetrahydrate, the barrier salt having moderate or high water activity.

2. The granule of claim 1 wherein the barrier salt is coated over the protein core in one or more layers.

3. The granule of claim 1 wherein the protein core comprises an enzyme.

4. The granule of claim 1 wherein the moderate or high water activity is greater than 0.25.

5. The granule of claim 1 wherein the moderate or high water activity is greater than 0.30.

6. The granule of claim 1 wherein the moderate or high water activity is greater than 0.35.

7. The granule of claim 1 wherein the barier salt is magnesium sulfate heptahydrate.

8. The granule of claim 1 wherein the barrier salt is trisodium citrate dihydrate.

9. A granule having moderate to high water activity, the granule comprising:

a seed;

an enzyme layer coated onto the seed;

a hydrated barrier salt coated onto the enzyme layer; and an outer coating over the hydrated barrier salt layer, wherein the hydrated barrier salt impedes transport of water into the granule.

10. The granule of claim 9, wherein the hydrated barrier salt layer has moderate or high water activity greater than 0.25.

11. The granule of claim 9 wherein the hydrated barrier salt has moderate or high water activity greater than 0.30.

12. The granule of claim 9 wherein the hydrated barrier salt has moderate or high water activity greater than 0.35.

13. The granule of claim 9 further comprising a hydrated barrier salt in the enzyme layer.

14. The granule of claim 9, wherein the hydrated barrier salt is selected from the group consisting of magnesium sulfate heptahydrate, zinc sulfate heptahydrate, sodium phosphate dibasic heptahydrate, magnesium nitrate hexahydrate, sodium citrate dihydrate and magnesium acetate tetrahydrate.

15. The granule of claim 9 wherein the hydrated barrier salt is magnesium sulfate heptahydrate.

16. The granule of claim 9 wherein the hydrated barrier salt is trisodium citrate dihydrate.

17. The granule of claim 9 wherein the hydrated barrier salt is coated onto the enzyme layer in one or more layers.

18. A method of producing the granule of claim 9 comprising:

a) providing the seed coated with an enzyme layer;

b) coating the hydrated barrier salt onto the enzyme layer; and c) appylng the outer coating over the hydrated barrier salt.

19. The method of claim 18 wherein b) further comprises coating at 50° C. or slightly below 50° C.

20. The method of claim 18 wherein b) further comprises coating at an outlet temperature of 40–50° C.

21. The method of claim 18 wherein step b) comprises coating the hydrated barrier salt onto the enzyme layer in one or more layers.

* * * * *

UNITED STATES PATENT AND TRADEMARK OFFICE
CERTIFICATE OF CORRECTION

PATENT NO.        : 6,602,841 B1
APPLICATION NO.   : 09/581717
DATED             : August 5, 2003
INVENTOR(S)       : Nathaniel T. Becker et al.

It is certified that error appears in the above-identified patent and that said Letters Patent is hereby corrected as shown below:

Claim 1, Column 8, Line 49, "dehydrate" should read -- dihydrate --.

Signed and Sealed this

Twenty-fifth Day of March, 2008

JON W. DUDAS
*Director of the United States Patent and Trademark Office*